United States Patent [19]

Shimano et al.

[11] Patent Number: 4,531,964
[45] Date of Patent: Jul. 30, 1985

[54] HETEROCYCLIC COMPOUND AND A HERBICIDAL COMPOSITION CONTAINING SAID COMPOUND

[75] Inventors: Shizuo Shimano, Ageo; Shinichi Kobayashi, Fuchu; Mikio Yanagi, Okegawa; Osamu Yamada; Mikio Saito, both of Ageo; Fumio Futatsuya, Ohmiya, all of Japan

[73] Assignee: Nippon Kayaku Kabushiki Kaisha, Tokyo, Japan

[21] Appl. No.: 527,493

[22] Filed: Aug. 29, 1983

[30] Foreign Application Priority Data

Sep. 13, 1982 [JP] Japan .................... 57-158228
Oct. 15, 1982 [JP] Japan .................... 57-175175

[51] Int. Cl.³ .................... A01N 43/50; C07D 471/04
[52] U.S. Cl. .................... 71/92; 71/94; 71/95; 546/121; 546/226; 548/302; 548/533
[58] Field of Search ............ 546/121, 226; 548/302, 548/533; 71/92, 94, 95

[56] References Cited

U.S. PATENT DOCUMENTS 3,958,976 5/1976 Goddard .................... 546/121
4,138,242 2/1979 Goddard .................... 546/121
4,439,229 3/1984 Swithenbank ............ 546/121

FOREIGN PATENT DOCUMENTS 2604989 8/1976 Fed. Rep. of Germany ...... 548/302

*Primary Examiner*—Henry R. Jiles
*Assistant Examiner*—Bernard I. Dentz
*Attorney, Agent, or Firm*—Henry C. Nields

[57] ABSTRACT

A compound of the formula:

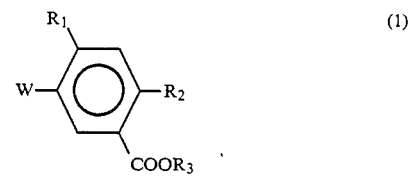

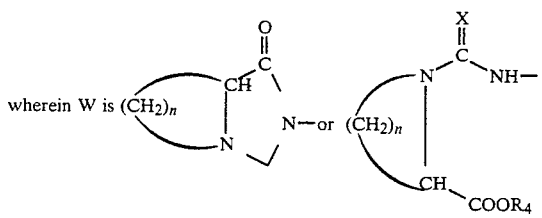

wherein $R_4$ is lower alkyl, X is oxygen or sulfur, and n is integer of 3 or 4; $R_1$ is hydrogen or halogen; $R_2$ is halogen; $R_3$ is hydrogen or $C_1$–$C_8$-alkyl which may have lower alkoxy; a herbicidal composition containing said compound as an effective component; a method for killing weeds using said compound; and processes for the production of said compound, are disclosed hereinafter.

11 Claims, No Drawings

HETEROCYCLIC COMPOUND AND A HERBICIDAL COMPOSITION CONTAINING SAID COMPOUND

DETAILED DESCRIPTION OF THE INVENTION

This invention relates to a compound of the formula:

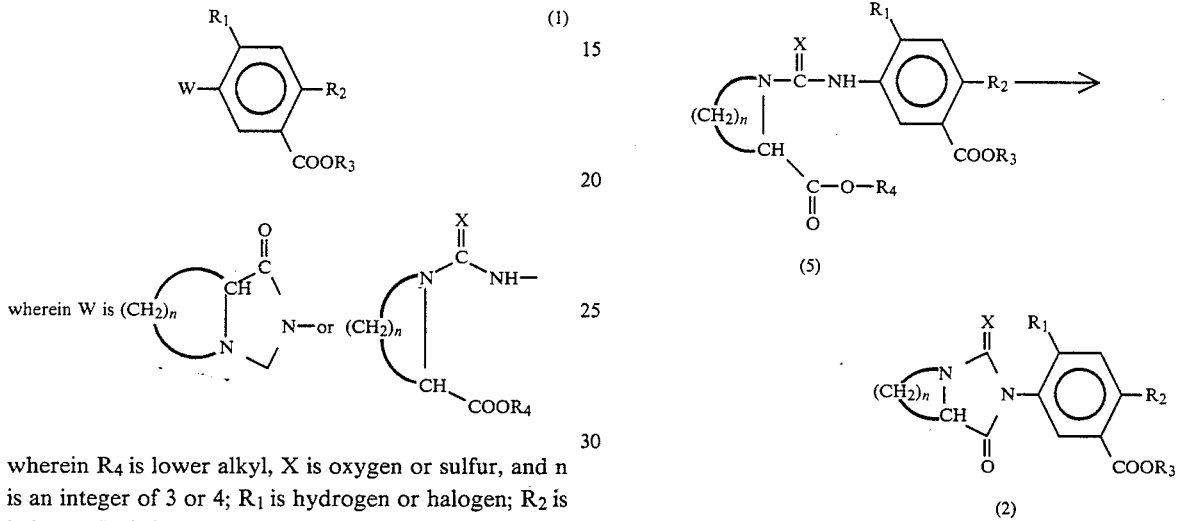

wherein $R_4$ is lower alkyl, X is oxygen or sulfur, and n is an integer of 3 or 4; $R_1$ is hydrogen or halogen; $R_2$ is halogen; $R_3$ is hydrogen or a $C_1$-$C_8$ alkyl which may be substituted with lower alkoxy, a herbicidal composition containing said compound as an effective component, a method of killing weeds using said compound and processes for the production of said compound.

It is known that certain analogues to the compounds of this invention have a herbicidal activity. For example, Japanese Patent Kokai No. 95134/1976 and U.S. Pat. Nos. 3,958,976 and 4,138,242 disclose compounds which exhibit a herbicidal activity.

We have found that the compound of the formula (1) exhibits extremely potent herbicidal activities with very low phytotoxicity to crops and hence can provide practical herbicides.

The compound of the formula (1) exhibits excellent herbicidal effect in a paddy field at a low dosage not only against annual weeds such as barnyard grasses and broadleaf weeds, but also against perennial weeds such as mizugayatsuri, bulrush, water chestnut, needle spikerush and arrowhead. The compound of the formula (1) also shows a good herbicidal effect by both pre- and post-emergence treatments in an up-land, especially against broadleaf weeds as those of amaranth, goosefoot and buckwheat families at a low dosage.

Furtheremore, the compound of the formula (1) is hardly phytotoxic to crops such as rice, wheat, oat, corn, soybean, cotton and sunflower.

The compounds represented by the formula (1) can be prepared in the following manner:

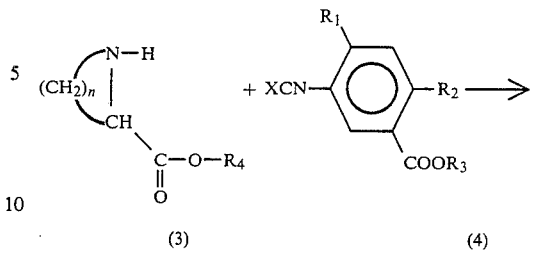

For example, a compound of the formula (3) (wherein $R_4$ is hydrogen or lower alkyl and n is an integer of 3 or 4), e.g., proline, pipecolic acid or an ester thereof, can be reacted with a substituted phenyl isocyanate or a substituted phenyl isothiocyanate of the formula (4) (wherein $R_1$, $R_2$, $R_3$ and X are the same as those set forth in the formula (1)) to obtain a compound of the formula (5) (wherein $R_1$, $R_2$, $R_3$, $R_4$ and X are the same as those set forth in the formula (1)), which corresponds to the compound of the formula (1) wherein W is a group of the formula:

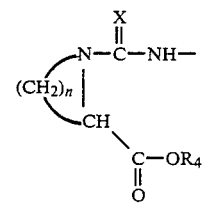

Then the obtained compound of the formula (5) may be recovered or the reaction may be allowed to proceed without recovering said compound. Thus obtained compound of the formula (5) can be cyclized by heat treatment or the addition of an appropriate acid catalyst to form a compound of the formula (2), which corresponds to the compound of the formula (1) wherein W is a group of the formula:

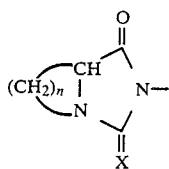

Though the reaction can be conducted in the absence of solvent, it is advantageously conducted in the presence of an inert solvent. Generally, the reaction proceeds in the temperature range of 0° to 150° C. When X is oxygen, the compound of the formula (5) can be obtained at a reaction temperature of 0° to 50° C. and can often be cyclized by heating at a higher temperature. Also the compound can be easily cyclized in the presence of an acid catalyst. In that case, although the cyclization proceeds without heating, the reaction is accelerated by heating. The compound, where X is sulfur, can be cyclized in a similar manner to that described above. The reaction time is generally 30 minutes to three hours.

Examples of said inert solvents include aromatic hydrocarbons such as benzene, toluene, xylene and chlorobenzene; aliphatic hydrocarbons such as n-hexane, n-butane and petroleum ether; alicyclic hydrocarbons such as cyclohexane; halogenated hydrocarbons such as chloroform, carbon tetrachloride and perchloroethylene; ketones such as acetone and methyl ethyl ketone; ethers such as ethyl ether, tetrahydrofuran and dioxane; alcohols such as methanol and ethanol; esters such as ethyl acetate; amides such as dimethylformamide; and water.

Examples of said acid catalysts are p-toluenesulfonic acid, sulfuric acid and hydrochloric acid.

Examples of the halogen in the formula (1) are chlorine, bromine and fluorine.

Examples of the lower alkoxy are methoxy and ethoxy.

Examples of $C_1$–$C_8$ alkyl are methyl, ethyl, n-propyl, isopropyl, n-butyl, sec-butyl, isobutyl, n-pentyl, n-hexyl, n-heptyl, n-octyl, 2-ethylhexyl and 1,3-dimethylbutyl.

Examples of the lower alkyl represented by $R_4$ in the formula (4) include $C_1$–$C_4$ alkyls such as methyl, ethyl, n-propyl, isopropyl, n-butyl and sec-butyl.

The compounds of the formula (3) used as starting materials are known compounds. The compounds of the formula (4) can be prepared by reacting a substituted aniline of formula (6) with a phosgene or a thiophosgene of the formula (7) or trichloromethyl chloroformate of the formula (8),

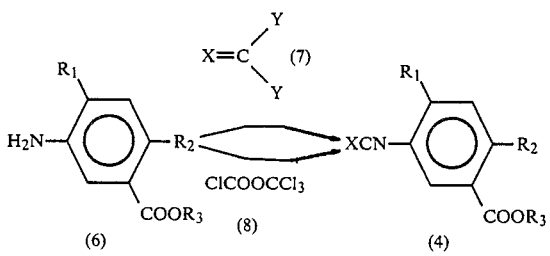

wherein $R_1$, $R_2$ and $R_3$ are the same as those set forth in the formula (1), X is oxygen or sulfur, and Y is halogen.

Though the reaction can be conducted in the absence of solvent, it is advantageously conducted in the presence of an inert solvent. The reaction is generally conducted at a temperature of $-20°$ C. to the boiling point of the reaction mixture, preferably 0° to 120° C. Preferably, the reaction is conducted under normal pressure, but it is also possible to conduct the reaction under elevated or reduced pressure.

Preferred compounds of the formula (1) of this invention are those where $R_1$ is chlorine or fluorine, $R_2$ is chlorine or bromine and $R_3$ is a $C_2$–$C_4$ alkyl group, when W in the formula (1) is a group of the formula:

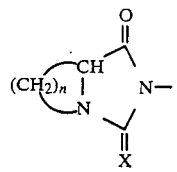

wherein n is an integer of 3 or 4 and X is oxygen or sulfur.

In another aspect, preferred compounds of the formula (1) are those where $R_1$ is chlorine or fluorine, $R_2$ is chlorine or bromine, and $R_3$ is a $C_2$–$C_4$ alkyl, when W is a group of the formula:

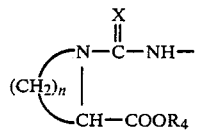

wherein $R_4$ is a $C_2$–$C_4$ alkyl, n is an integer of 3 or 4, and X is oxygen or sulfur. The most preferred compounds of the formula (1) are

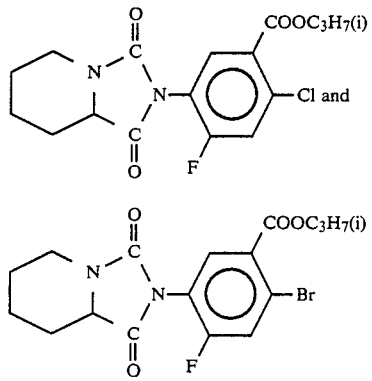

The following synthesis examples are provided to illustrate the preparation of the compounds of this invention.

SYNTHESIS EXAMPLE 1

3-(4-Chloro-3-n-propoxycarbonylphenyl)-1,5-trimethylene-2-thiohydantoin (Compound No. 1).

2.6 g (0.01 mol) of 4-chloro-3-n-propoxy-carbonylphenyl isothiocyanate were added to a solution of 1.5 g (0.01 mol) of ethyl ester of proline dissolved in 30 ml of benzene. The mixture was stirred at room temperature for an hour and then concentrated. The resulting oily substance was purified by means of silica gel column chromatography to give 1.6 g (yield 45%) of the desired product as pale yellow crystals with a melting point of 93°–95° C.

Elemental analysis (%) for $C_{16}H_{17}ClN_2O_3S$: calculated: C: 54.46, H: 4.85, N: 7.93; found: C: 54.74, H: 4.94, N: 8.05.

The desired product can be obtained also by using hydrochloride of proline ethyl ester together with triethylamine in place of the free ester.

SYNTHESIS EXAMPLE 2

3-(2-Fluoro-4-chloro-5-isopropoxycarbonylphenyl)-1,5-tetramethylenehydantoin (Compound No. 7).

5.15 g (0.02 mol) of 2-fluoro-4-chloro-5-isopropoxycarbonylphenyl isocyanate were added to a solution of 3.2 g (0.02 mol) of ethyl pipecolate dissolved in 30 ml of benzene. The mixture was stirred at a temperature of 40° to 50° C. for an hour, washed with water, dried over anhydrous sodium sulfate, and then concentrated. The resulting crystals were recrystallized from a mixed solvent of n-hexane and ethyl acetate to give 6.9 g (yield 83.2%) of 1-(2-fluoro-4-chloro-5-isopropoxycarbonylphenyl)aminocarbonyl-2-ethoxycarbonylpiperidine. This compound was dissolved in 70 ml of toluene and hydrogen chloride was blown thereinto. The mixture was stirred at room temperature for three hours, washed with a saturated solution of sodium hydrogen carbonate, washed with water, dried over anhydrous sodium sulfate and then concentrated. The resulting crystals were recrystallized from a mixed solvent of toluene and ethyl acetate to give 2.6 g (yield 71.9%) of the desired product as white crystals with a melting point of 128°–129° C.

Elemental analysis (%) for $C_{17}H_{18}ClN_2O_4$: calculated: C: 55.36, H: 4.91, N: 7.59; found: C: 55.58, H: 4.86, N: 7.70.

SYNTHESIS EXAMPLE 3

3-(4-Chloro-3-methoxycarbonylphenyl)-1,5-tetramethylene-2-thiohydantoin (Compound No. 10).

2.3 g (0.01 mol) of 4-chloro-3-methoxy-carbonylphenylisothiocyanate were added to a solution of 1.6 g (0.01 mol) of ethyl pipecolate dissolved in 30 ml of benzene. The mixture was stirred at room temperature for an hour, and then concentrated. The resulting crystals were recrystallized from a mixed solvent of toluene and ethyl acetate to give 2.4 g (yield 71%) of the desired product as pale yellow crystals with a melting point of 167°–169° C.

Elemental Analysis (%) for $C_{15}H_{15}ClN_2O_3S$: calculated: C: 53.17, H: 4.46, N: 8.26; found: C: 53.39, H: 4.44, N: 8.14.

SYNTHESIS EXAMPLE 4

3-(2-Fluoro-4-chloro-5-sec-butoxy-carbonylphenyl)-1,5-tetramethylene-2-thiohydantoin (Compound No. 16).

4 g (0.0139 mol) of 2-fluoro-4-chloro-5-sec-butoxyphenyl isothiocyanate were added to a solution of 2.1 g (0.0139 mol) of ethyl pipecolate dissolved in 30 ml of benzene. The mixture was stirred at room temperature for an hour, washed with water, dried over anhydrous sodium sulfate and then concentrated. The resulting oily substance was purified by means of silica gel column chromatography to give 3.3 g (yield 59.5%) of the desired product as a pale brown crystal with a melting point of 86°–88° C.

Elemental Analysis (%) for $C_{18}H_{20}FClN_2O_3S$: calculated: C: 54.20, H: 5.05, N: 7.02; found: C: 54.42, H: 5.12, N: 7.03.

SYNTHESIS EXAMPLE 5

3-(2-Fluoro-4-chloro-5-methoxyethoxycarbonylphenyl)-1,5-tetramethylene-2-thiohydantoin (Compound No. 19).

5.8 g (0.02 mol) of 2-fluoro-4-chloro-5-methoxyethoxycarbonylphenyl isothiocyanate were added to a solution of 3.2 g (0.02 mol) of ethyl pipecolate dissolved in 50 ml of benzene. The mixture was stirred with heating at a temperature of 40° to 50° C. for an hour, washed with water, dried over anhydrous sodium sulfate, and then concentrated. The resulting oily substance was purified by means of silica gel column chromatography to give 4.6 g (yield 57.4%) of the desired product as a pale brown crystal with refractive index of $n_D^{25}$ 1.5729.

Elemental Analysis (%) for $C_{17}H_{18}FClN_2O_4S$: calculated: C: 50.94, H: 4.53, N: 6.98; found: C: 51.07, H: 4.45, N: 7.21.

Other compounds prepared by the above-mentioned method are given in Table 1.

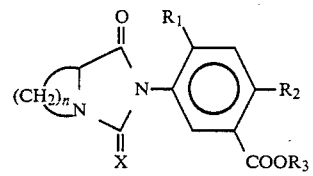

TABLE 1

| Compound No. | n | X | $R_1$ | $R_2$ | $R_3$ | m.p. (°C.) or refractive index | Appearance |
|---|---|---|---|---|---|---|---|
| 1 | 3 | S | H | Cl | $C_3H_7(n)$ | 93–95 | pale yellow crystal |
| 2 | 4 | O | F | Cl | $CH_3$ | glassy | colorless |
| 3 | 4 | O | F | Cl | $C_2H_5$ | 102–103 | white crystal |
| 4 | 4 | O | H | Cl | $C_3H_7(i)$ | 109–110 | " |
| 5 | 4 | O | H | Br | $C_3H_7(i)$ | 121–123 | pale yellow crystal |
| 6 | 4 | O | Cl | Cl | $C_3H_7(i)$ | $n_D^{25}$1.5545 | pale yellow oil |
| 7 | 4 | O | F | Cl | $C_3H_7(i)$ | 128–129 | white crystal |
| 8 | 4 | O | F | Br | $C_3H_7(i)$ | 116–118 | pale yellow crystal |
| 9 | 4 | O | H | Cl | $C_4H_9(sec)$ | 76–79 | white crystal |
| 10 | 4 | S | H | Cl | $CH_3$ | 167–169 | pale yellow crystal |
| 11 | 4 | S | H | Cl | $C_2H_5$ | 143–145 | brown crystal |
| 12 | 4 | S | H | Cl | $C_3H_7(n)$ | 103–104 | pale yellow crystal |
| 13 | 4 | S | H | Cl | $C_3H_7(i)$ | 137.5–139.5 | white crystal |
| 14 | 4 | S | H | Br | $C_3H_7(i)$ | 113–114 | pale yellow crystal |
| 15 | 4 | S | F | Cl | $C_3H_7(i)$ | 123–125 | pale brown crystal |
| 16 | 4 | S | F | Cl | $C_4H_9(sec)$ | 86–88 | " |

TABLE 1-continued

| Compound No. | n | X | R₁ | R₂ | R₃ | m.p. (°C.) or refractive index | Appearance |
|---|---|---|---|---|---|---|---|
| 18 | 4 | S | F | Cl | CH(CH₃)CH₂CH(CH₃)CH₃ | $n_D^{25}1.5660$ | pale yellow oil |
| 19 | 4 | S | F | Cl | CH₂CH₂OCH₃ | $n_D^{25}1.5729$ | pale yellow oil |
| 20 | 4 | S | F | Cl | CH₂CH(C₂H₅)(CH₂)₃CH₃ | $n_D^{25}1.5511$ | " |
| 21 | 4 | S | Cl | Cl | C₃H₇(i) | 57–59 | pale yellow crystal |
| 22 | 4 | S | F | Cl | C₂H₅ | 139–140 | pale yellow crystal |
| 23 | 4 | S | F | Br | C₃H₇(i) | $n_D^{25}1.5700$ | brown oil |
| 24 | 4 | O | F | Cl | CH₂CH₂OCH₃ | $n_D^{25}1.5485$ | colorless oil |
| 25 | 4 | O | F | Cl | CH₂CH(C₂H₅)(CH₂)₃CH₃ | $n_D^{25}1.5302$ | pale yellow oil |
| 26 | 4 | O | F | Cl | CH₂CH₂CH(CH₃)CH₃ | $n_D^{25}1.5330$ | pale brown oil |
| 27 | 4 | O | F | Cl | CH₂(CH₂)₄CH₃ | $n_D^{25}1.5309$ | " |
| 28 | 4 | O | F | Cl | CH(CH₂CH₃)CH₂CH₃ | $n_D^{25}1.5310$ | brown oil |

SYNTHESIS EXAMPLE 6

1-(2-Fluoro-4-chloro-5-ethoxycarbonylphenylaminocarbonyl)-2-ethoxycarbonylpyrrolidine (Compound No. 29).

3.61 g (0.02 mol) of proline ethyl ester hydrochloride were mixed with 100 ml of toluene and 2.8 ml (0.02 mol) of triethylamine were added thereto. Then 4.87 g (0.02 mol) of 2-fluoro-4-chloro-5-ethoxycarbonylphenyl isocyanate were added thereto. The mixture was stirred at room temperature for two hours, washed with water, dried over anhydrous sodium sulfate, and then concentrated. The resulting crystal was recrystallized from a mixed solvent of hexane and toluene to give 6.2 g (yield 80.1%) of the desired product as white crystals with a melting point of 95°–95.5° C.

Elemental analysis (%) for $C_{17}H_{20}ClFN_2O_5$: calculated: C: 52.78, H: 5.21, N: 7.24; found: C: 53.00, H: 5.27, N: 7.29.

SYNTHESIS EXAMPLE 7

1-(4-Chloro-3-isopropoxycarbonylphenylaminothiocarbonyl)-2-ethoxycarbonylpyrrolidine (Compound No. 33).

1.8 g (0.01 mol) of proline ethyl ester hydrochloride and 1.0 g of triethylamine were added dropwise to 30 ml of benzene and 2.6 g (0.01 mol) of 4-chloro-3-isopropoxycarbonylphenyl isothiocyanate were added thereto. The mixture was stirred at room temperature for an hour, washed with water, dried over anhydrous sodium sulfate, and then concentrated. The residue was purified by means of silica gel column chromatography to give 2.5 g (yield 63%) of the desired product as a yellow glassy substance.

Elemental analysis (%) for $C_{18}H_{23}ClN_2O_4S$: calculated: C: 54.20, H: 5.81, N: 7.02; found: C: 54.47, H: 5.95, N: 7.08.

SYNTHESIS EXAMPLE 8

1-(4-Chloro-2-fluoro-5-isopropoxycarbonylphenylaminocarbonyl)-2-ethoxycarbonylpiperidine (Compound No. 36).

5.15 g (0.02 mol) of 4-chloro-2-fluoro-5-isopropoxycarbonylphenyl isocyanate were added to a solution of 3.31 g (0.02 mol) of ethyl pipecolate (95% purity) dissolved in 30 ml of benzene. The mixture was stirred at room temperature for an hour, washed with water, dried over anhydrous sodium sulfate, and then concentrated. The resulting crystal was recrystallized from a mixed solvent of hexane, toluene and ethyl acetate to give 6.9 g (yield 83.2%) of the desired product as white crystals with a melting point of 83°–85° C.

Elemental analysis (%) for $C_{19}H_{24}ClFN_2O_5$: calculated: C: 55.00, H: 5.83, N: 6.75; found: C: 55.25, H: 5.95, N: 6.78.

Other compounds prepared by the above-mentioned method are given in Table 2.

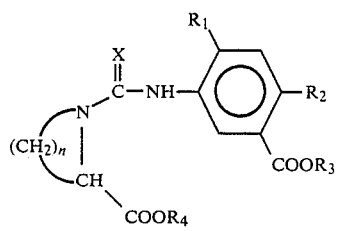

TABLE 2

| Compound No. | n | X | R₁ | R₂ | R₃ | R₄ | m.p. (°C.) or refractive index | Appearance |
| --- | --- | --- | --- | --- | --- | --- | --- | --- |
| 29 | 3 | O | F | Cl | C$_2$H$_5$ | C$_2$H$_5$ | 95–95.5 | white crystal |
| 30 | 3 | O | F | Cl | C$_3$H$_7$(i) | " | 113–115 | " |
| 31 | 3 | O | H | Cl | " | " | n$_D^{25}$1.5425 | pale yellow oil |
| 32 | 3 | O | H | Br | " | " | n$_D^{25}$1.511 | " |
| 33 | 3 | S | H | Cl | " | " | glassy | yellow |
| 34 | 4 | O | F | Cl | CH$_3$ | " | 117–118 | white crystal |
| 35 | 4 | O | F | Cl | C$_2$H$_5$ | " | 96.5–97 | " |
| 36 | 4 | O | F | Cl | C$_3$H$_7$(i) | " | 83–85 | " |
| 37 | 4 | O | F | Br | " | " | 74–76 | " |
| 38 | 4 | O | Cl | Cl | " | " | 79.5–81 | " |
| 39 | 3 | S | F | Cl | CHCH$_2$CHCH$_3$<br>   \|       \|<br>CH$_3$  CH$_3$ | " | n$_D^{25}$1.5470 | pale yellow oil |
| 40 | 3 | O | F | Cl | CH$_2$CH$_2$OCH$_3$ | " | 100–102 | white crystal |
| 41 | 3 | S | F | Cl | CH$_2$CH(CH$_2$)$_3$CH$_3$<br>      \|<br>    C$_2$H$_5$ | " | n$_D^{25}$1.5515 | yellow oil |
| 42 | 4 | O | F | Cl | C$_3$H$_7$(i) | C$_3$H$_7$(i) | n$_D^{25}$1.5150 | pale yellow oil |
| 43 | 4 | O | F | Cl | " | C$_3$H$_7$(n) | n$_D^{25}$1.5241 | colorless oil |
| 44 | 4 | O | F | Cl | " | C$_4$H$_9$(n) | 63–65 | pale yellow oil |

The following referential examples illustrate the synthesis of a substituted phenyl isocyanate and a substituted phenyl isothiocyanate.

REFERENTIAL EXAMPLE 1

Preparation of 4-chloro-2-fluoro-5-isopropoxycarbonylphenyl isocyanate.

5.4 ml (0.045 mol) of trichloromethyl chloroformate were added to 30 ml of ethyl acetate. The resulting solution was cooled to 0° C. A solution of 13.9 g (0.06 mol) of 4-chloro-2-fluoro-5-isopropoxycarbonylaniline in 25 ml of ethyl acetate were added dropwise to the above cooled solution over a period of 15 minutes. The mixture was stirred at a temperature of 0° to 10° C. for an hour, and then refluxed for two hours. The reaction mixture was concentrated to give 15.45 g (yield 99.9%) of the desired product as nearly white crystals with a melting point of 41°–43° C.

REFERENTIAL EXAMPLE 2

Preparation of 2,4-dichloro-5-ethoxycarbonylphenyl isothiocyanate.

23.4 g (0.1 mol) of 2,4-dichloro-5-ethoxycarbonylaniline were dissolved in 80 ml of chloroform. The resulting solution was cooled to 10° C. or lower and 14.9 g (0.13 mol) of thiophosgene were added dropwise thereto. The mixture was stirred at room temperature for two hours, and then refluxed for three hours. The reaction mixture was concentrated to give 27 g (yield 97.7%) of the desired product as pale brown crystals with a melting point of 45°–46° C.

The herbicidal composition of the present invention can be used either alone or in the form of a formulation according to the purpose of its use. To promote or secure the effect, it is mixed with adjuvants to make formulations such as dust, micro granule, granule, wettable powder, flowable suspension concentrates and emulsion by means of usual procedures. These formulations are used, at the time of practical application, in the form as they are or diluted with water to desired concentration.

Those adjuvants mentioned above include carriers (diluents), extending agents, emulsifiers, wetting agents, dispersing agents, fixing agents and disintegrators.

As liquid carriers there can be used water, aromatic hydrocarbons such as toluene and xylene, alcohols such as methanol, butanol and glycol, ketones such as acetone, amides such as dimethylformamide, sulfoxides such as dimethylsulfoxide, methylnaphthalene, cyclohexane, animal and vegetable oils, fatty acids and their esters, etc. As solid carriers are used clay, kaolin, talc, diatomaceous earth, silica, calcium carbonate, montmorillonite, bentonite, feldspar, quartz, alumina, sawdust, etc.

As emulsifiers or dispersing agents surfactants are generally used. They include anionic, cationic, nonionic and amphoteric surfactants such as sodium salts of sulfated higher alcohol, stearyltrimethylammonium chloride, polyoxyethylenealkylphenylether and lauryl betaine. Wetting agents include sodium alkylnaphthalene sulfonate and ammonium polyoxyethylenealkylphenylether sulfate, fixing agents include polyvinyl alcohol, polyvinyl acetate and CMC, and disintegrators include sodium lignin sulfonate.

Any type of said formulations can be used not only alone, but also with fungicides, insecticides, plant growth regulators, acaricides, soil modifying agents or nematocides and further can be used in combination with fertilizers or other herbicides.

The content of a compound (active ingredient) of the present invention in the formulations varies with types of formulation, methods of application and other conditions, but generally it is 0.5 to 95 weight %, preferably 2 to 50 weight %, while the content of adjuvants is 5 to 99.5 weight %, preferably 50 to 98 weight %, though sometimes the compound can be used alone.

To be more precise, a preferable range of the content is shown as under.

|  | Compound (weight %) | Adjuvant (weight %) |
| --- | --- | --- |
| Dust | 0.5–10 | 90–99.5 |
| Emulsion | 20–80 | 20–80 |

-continued

|  | Compound (weight %) | Adjuvant (weight %) |
|---|---|---|
| Wettable powder | 20–80 | 20–80 |
| Granule and micro granule | 0.5–20 | 80–99.5 |
| Flowable suspension concentrate | 20–80 | 20–80 |

The formulations of the present invention can be directly applied to weeds or locus thereof.

A quantity to use of the formulations is different with kinds of the active ingredient and places of application, but generally it is within the range of 1 to 100 g, preferably 3 to 75 g, of the compound per are.

Detailed explanation will be made below on examples of formulations of the present invention and there the word "part" means part by weight.

FORMULATION EXAMPLE 1: Emulsion 35 parts of a mixture (1:1) of xylene and methylnaphthalene are added to 50 parts of Compound No. 2 to dissolve and the solution is further mixed with 15 parts of a mixture (8:2) of polyoxyethylenealkylphenylether and calcium alkylbenzenesulfonate to obtain an emulsion. It is diluted with water to use in a concentration of 0.01 to 1%.

FORMULATION EXAMPLE 2: Dust 5 parts of Compound No. 7 are mixed with 95 parts of clay and pulverized to obtain a dust. It is directly used for dusting.

FORMULATION EXAMPLE 3: Wettable powder 50 parts of Compound No. 8 are mixed with 10 parts of diatomaceous earth and 32 parts of kaolin and further uniformly blended with 8 parts of a mixture of sodium laurylsulfate and sodium 2,2'-dinaphthylmethanesulfonate, and finely pulverized to obtain a wettable powder.

FORMULATION EXAMPLE 4: Granule 5 parts of a fine dust of Compound No. 15 are extended for coating on 94.5 parts of grains (16 to 32 mesh) of silica to obtain a granule, by using a methanol solution of 0.5 parts of polyvinyl polyacetate as the binding agent in a proper mixer. The granule is scattered directly in up-land field and a paddy field.

FORMULATION EXAMPLE 5: Flowable suspension concentrates 40 parts of a fine powder of Compound 24, 10 parts of ethyleneglycolmonobutylether, 10 parts of a surfactant (mixture of trioxyalkylether, polyoxyethylenenonylphenylether and sodium alkylarylsulfonate), 3 parts of colloidal aluminium silicate hydrate and 22 parts of water are uniformly mixed and further blended under stirring in a homomixer for 20 minutes to obtain a flowable. It is diluted with water for use in a concentration of 0.02 to 1%.

The excellent herbicidal activity of a compound of the present invention will be illustrated in the following test examples.

Each test was carried out on 2-replication system and the test results are given in the average value.

TEST EXAMPLE 1: Pre-emergence treatment in flooded condition

A fixed amount of paddy field soil was filled in each Wagner pot sized 1/5,000 are to provide a condition similar to a paddy field and there was sown a fixed amount of seeds of barnyard grass, monochoria, toothcup, false pimpernal, waterstarwort and umbrella plant.

In addition tubers of arrowhead were buried 1 cm under the surface of soil at the rate of 3 pieces per pot and the pot was flooded with water 3 cm deep. Then the pot was applied with a diluted solution of the compound of the present invention at a rate of 6.25 to 50 g of the compound of the present invention per are.

Thirty days after the treatment the herbicidal activity was observed. The test results were classified on the following basis as shown in Table 3.

Herbicidal activity index:

| 5 | Complete weeding |
|---|---|
| 4 | up to 80% weeding |
| 3 | up to 60% weeding |
| 2 | up to 40% weeding |
| 1 | up to 20% weeding |
| 0 | no effect |

TABLE 3

Test Example 1:
Pre-emergence treatment under flooded condition

| Compound No. | Dosage g/a | Herbicidal activity | | | |
|---|---|---|---|---|---|
| | | Barnyard grass | Broadleaf (1) | Umbrellasedge (2) | Arrowhead |
| 2 | 25 | 3.5 | 5 | 5 | 5 |
| | 12.5 | 4 | 5 | 5 | 5 |
| | 6.25 | 5 | 5 | 5 | 5 |
| 3 | 25 | 5 | 5 | 5 | 5 |
| | 12.5 | 5 | 5 | 5 | 5 |
| | 6.25 | 5 | 5 | 5 | 5 |
| 4 | 25 | 5 | 5 | 5 | 5 |
| | 12.5 | 5 | 5 | 5 | 4.5 |
| | 6.25 | 5 | 5 | 5 | 4 |
| 5 | 25 | 5 | 5 | 5 | 4 |
| | 12.5 | 5 | 5 | 5 | 5 |
| | 6.25 | 5 | 5 | 5 | 5 |
| 6 | 25 | 5 | 5 | 5 | 5 |
| | 12.5 | 5 | 5 | 5 | 5 |
| | 6.25 | 5 | 5 | 5 | 4.5 |
| 7 | 25 | 5 | 5 | 5 | 5 |
| | 12.5 | 5 | 5 | 5 | 5 |
| | 6.25 | 5 | 5 | 5 | 5 |
| 8 | 25 | 5 | 5 | 5 | 5 |
| | 12.5 | 5 | 5 | 5 | 5 |
| | 6.25 | 5 | 5 | 5 | 5 |
| 10 | 25 | 5 | 5 | 5 | 5 |
| | 12.5 | 5 | 5 | 5 | 5 |
| | 6.25 | 5 | 5 | 5 | 2 |
| 11 | 25 | 5 | 5 | 5 | 5 |
| | 12.5 | 5 | 5 | 5 | 5 |
| | 6.25 | 5 | 5 | 5 | 5 |
| 12 | 25 | 5 | 5 | 5 | 5 |
| | 12.5 | 5 | 5 | 5 | 5 |
| | 6.25 | 5 | 5 | 5 | 5 |
| 13 | 25 | 5 | 5 | 5 | 5 |
| | 12.5 | 5 | 5 | 5 | 5 |
| | 6.25 | 5 | 5 | 5 | 5 |
| 14 | 25 | 5 | 5 | 5 | 5 |
| | 12.5 | 5 | 5 | 5 | 5 |
| | 6.25 | 5 | 5 | 5 | 3 |
| 15 | 25 | 5 | 5 | 5 | 5 |
| | 12.5 | 5 | 5 | 5 | 5 |
| | 6.25 | 5 | 5 | 5 | 4.5 |
| 16 | 25 | 5 | 5 | 5 | 5 |
| | 12.5 | 5 | 5 | 5 | 5 |
| | 6.25 | 5 | 5 | 5 | 4.5 |
| 18 | 25 | 5 | 5 | 5 | 5 |
| | 12.5 | 5 | 5 | 5 | 5 |
| | 6.25 | 5 | 5 | 5 | 5 |
| 20 | 25 | 5 | 5 | 5 | 4 |

TABLE 3-continued

Test Example 1:
Pre-emergence treatment under flooded condition

| Compound No. | Dosage g/a | Barnyard grass | Broadleaf (1) | Umbrella-sedge (2) | Arrowhead |
|---|---|---|---|---|---|
|  | 12.5 | 5 | 5 | 5 | 3 |
|  | 6.25 | 5 | 5 | 5 | 2 |
| 21 | 25 | 5 | 5 | 5 | 5 |
|  | 12.5 | 5 | 5 | 5 | 5 |
|  | 6.25 | 5 | 5 | 5 | 5 |
| 29 | 25 | 4 | 5 | 5 | 4.5 |
|  | 12.5 | 3 | 4 | 4 | 3 |
| 30 | 25 | 5 | 5 | 5 | 5 |
|  | 12.5 | 4.5 | 5 | 5 | 5 |
| 31 | 25 | 5 | 5 | 5 | 5 |
|  | 12.5 | 5 | 4 | 4 | 3 |
| 32 | 50 | 5 | 5 | 5 | 5 |
|  | 25 | 4 | 5 | 5 | 4.5 |
| 33 | 25 | 4.5 | 5 | 5 | 5 |
|  | 12.5 | 4 | 5 | 5 | 4.5 |
| 35 | 25 | 5 | 5 | 5 | 5 |
|  | 12.5 | 5 | 5 | 5 | 5 |
| Control A | 50 | 1 | 1 | 0 | 0 |
|  | 25 | 0 | 0 | 0 | 0 |

Remarks
(1) Broadleaf: Mixture of barnyard grass, toothcup, false pimpernel, waterstarwort.
(2) Umbrella-sedge: Umbrella plant
Control A

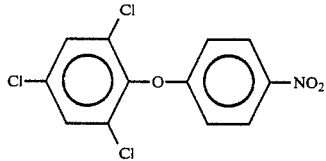

TEST EXAMPLE 2: Post-emergence treatment in flooded condition

A fixed amount of paddy field soil was filled in each Wagner pot sized 1/5,000 are to provide a condition similar to a paddy field and there was sown a fixed amount of seeds of barnyard grass, monochoria, toothcup, false pimpernel, waterstarwort and umbrella plant.

In addition tubers of arrowhead were buried 1 cm under the surface of soil at the rate of 3 pieces per pot, three 2.5-leaf stage rice seedlings (variety: Nihonbare) were transplanted from a nursery, the pot was flooded with water 3 cm deep and then placed in a greenhouse.

When the weeds grew to reach 2 to 3-leaf stage, a diluted solution of the compound of the present invention, was applied to the flood at a rate of 12.5 to 50 g of the compound of the present invention per are.

After 30 days from the treatment with the diluted solution, the herbicidal activity and the phytotoxicity against paddy rice were observed. The obtained results are shown in Table 4. The classification basis of the herbicidal activity is the same with Test Example 1, and that of the phytotoxicity is as follows:

−: no damage
+: slight damage
++: some damage
+++: moderate damage
++++: heavy damage
X: complete death.

TABLE 4

Test Example 2:
Post emergence treatment in flooded condition

| Compound No. | Dosage g/a | Barnyard grass | Broadleaf (1) | Umbrella-sedge (2) | Arrowhead | Phytotoxicity against rice |
|---|---|---|---|---|---|---|
| 1 | 25 | 4.5 | 5 | 5 | 4 | − |
|  | 12.5 | 4 | 5 | 5 | 3 | − |
|  | 6.25 | 3.5 | 5 | 5 | 2 | − |
| 4 | 25 | 5 | 5 | 5 | 5 | ++ |
|  | 12.5 | 5 | 5 | 5 | 4.5 | + |
|  | 6.25 | 5 | 5 | 5 | 4 | − |
| 6 | 25 | 5 | 5 | 5 | 5 | ++ |
|  | 12.5 | 5 | 5 | 5 | 5 | + |
|  | 6.25 | 5 | 5 | 5 | 4 | − |
| 9 | 25 | 5 | 5 | 5 | 5 | + |
|  | 12.5 | 5 | 5 | 5 | 4 | − |
|  | 6.25 | 5 | 5 | 5 | 2 | − |
| 10 | 25 | 5 | 5 | 5 | 5 | ++ |
|  | 12.5 | 5 | 5 | 5 | 5 | + |
|  | 6.25 | 5 | 5 | 5 | 2 | + |
| 11 | 25 | 5 | 5 | 5 | 5 | − |
|  | 12.5 | 5 | 5 | 5 | 5 | − |
|  | 6.25 | 5 | 5 | 5 | 5 | − |
| 12 | 25 | 5 | 5 | 5 | 5 | ++ |
|  | 12.5 | 5 | 5 | 5 | 5 | + |
|  | 6.25 | 5 | 5 | 5 | 5 | − |
| 15 | 25 | 5 | 5 | 5 | 5 | + |
|  | 12.5 | 5 | 5 | 5 | 5 | ± |
|  | 6.25 | 5 | 5 | 5 | 4.5 | − |
| 16 | 25 | 5 | 5 | 5 | 5 | − |
|  | 12.5 | 5 | 5 | 5 | 5 | − |
|  | 6.25 | 5 | 5 | 5 | 4.5 | − |
| 20 | 25 | 5 | 5 | 5 | 5 | − |
|  | 12.5 | 5 | 5 | 5 | 5 | − |
|  | 6.25 | 5 | 5 | 5 | 5 | − |
| 21 | 25 | 5 | 5 | 5 | 5 | + |
|  | 12.5 | 5 | 5 | 5 | 5 | ± |
|  | 6.25 | 5 | 5 | 5 | 5 | − |
| 29 | 25 | 5 | 5 | 5 | 5 | ++ |
|  | 12.5 | 5 | 5 | 5 | 5 | + |
|  | 6.25 | 5 | 5 | 5 | 5 | − |
| 30 | 25 | 5 | 5 | 5 | 3 | ++ |
|  | 12.5 | 5 | 5 | 5 | 5 | + |
|  | 6.25 | 5 | 5 | 5 | 5 | − |
| 31 | 25 | 5 | 5 | 5 | 4 | + |
|  | 12.5 | 4 | 5 | 5 | 3 | − |
|  | 6.25 | 2 | 3 | 3 | 2 | − |
| 32 | 25 | 5 | 5 | 5 | 5 | + |
|  | 12.5 | 5 | 5 | 5 | 3.5 | ± |
|  | 6.25 | 5 | 5 | 5 | 2 | − |
| 33 | 25 | 5 | 5 | 5 | 5 | − |
|  | 12.5 | 5 | 5 | 5 | 4.5 | − |
|  | 6.25 | 4.5 | 5 | 5 | 3.5 | − |
| 34 | 25 | 5 | 5 | 5 | 5 | ++ |
|  | 12.5 | 5 | 5 | 5 | 5 | + |
|  | 6.25 | 5 | 5 | 5 | 5 | − |
| 35 | 25 | 5 | 5 | 5 | 5 | ++ |
|  | 12.5 | 5 | 5 | 5 | 5 | + |
|  | 6.25 | 5 | 5 | 5 | 5 | − |
| 36 | 25 | 5 | 5 | 5 | 5 | ++ |
|  | 12.5 | 5 | 5 | 5 | 5 | + |
|  | 6.25 | 5 | 5 | 5 | 5 | − |
| 37 | 25 | 5 | 5 | 5 | 5 | ++ |
|  | 12.5 | 5 | 5 | 5 | 5 | + |
|  | 6.25 | 5 | 5 | 5 | 5 | − |
| 39 | 25 | 5 | 5 | 5 | 5 | + |
|  | 12.5 | 5 | 5 | 5 | 4.5 | − |
|  | 6.25 | 4.5 | 5 | 5 | 4 | − |
| 40 | 25 | 5 | 5 | 5 | 5 | − |
|  | 12.5 | 5 | 5 | 5 | 5 | − |
|  | 6.25 | 5 | 5 | 5 | 5 | − |
| 41 | 25 | 5 | 5 | 5 | 5 | − |
|  | 12.5 | 5 | 5 | 5 | 5 | − |
|  | 6.25 | 4 | 5 | 5 | 4.5 | − |
| Control | 25 | 3 | 4 | 3 | 0 | + |

TABLE 4-continued

Test Example 2:
Post emergence treatment in flooded condition

| Compound No. | Dosage g/a | Barnyard grass | Broadleaf (1) | Umbrella-sedge (2) | Arrowhead | Phytotoxicity against rice |
|---|---|---|---|---|---|---|
| A | 12.5 | 1 | 2 | 0 | 0 | — |

Remarks
(1) Broadleaf: Mixture of barnyard grass, toothcup, false pimpernel, waterstarwort.
(2) Umbrella-sedge: Umbrella plant
Control A

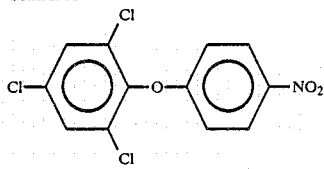

TEST EXAMPLE 3: Test on perennial weeds in a paddy field

Wagner pots sized 1/5,000 are were filled with a fixed amount of paddy field soil to provide a condition similar to a paddy field and there are sown a fixed amount of seeds of bulrush. In addition tubers of mizugayatsuri and water chestnut were buried 3 cm under the surface of soil at the rate of 3 pieces per pot and then the pot was flooded with water 3 cm deep.

The pre-emergence treatment was conducted on the second day after seeds and tubers of the weeds were put into soil, while the post-emergence treatment was effected at 2-leaf stage of bulrush, 2 to 3-leaf stage of mizugayatsuri and the time when water chestnut grew 5 to 6 cm high, at each time a diluted solution of the compound of the present invention was applied to the flood at a rate of 6.25 to 50 g of the compound of the present invention per are.

The herbicidal activity was observed on 30th day after each treatment and the test results are shown in Table 5. The judging standard of the results is the same with Test Example 1.

TABLE 5

Test Example 3:
Test on perennial weeds in paddy field

| Compound No. | Dosage g/a | Pre-emergence Water chestnut | Pre-emergence Mizugayatsuri | Post emergence Water chestnut | Post emergence Mizugayatsuri |
|---|---|---|---|---|---|
| 29 | 50 | 5 | 5 | 4.75 | 4.75 |
|  | 25 | 3 | 3 | 4 | 4 |
| 30 | 25 | 5 | 5 | 5 | 5 |
|  | 12.5 | 5 | 5 | 5 | 5 |
|  | 6.25 | 4.5 | 4.5 | 4 | 4 |
| 32 | 25 | 5 | 5 | 5 | 5 |
|  | 12.5 | 4 | 4 | 3 | 3 |
|  | 6.25 | 2 | 2 | 2 | 2 |
| 33 | 50 | 5 | 5 | 5 | 5 |
|  | 25 | 4 | 4 | 4 | 3.5 |
|  | 12.5 | 2 | 3 | 2 | 2 |
| 35 | 25 | 5 | 5 | 5 | 5 |
|  | 12.5 | 5 | 5 | 5 | 5 |
|  | 6.25 | 5 | 5 | 5 | 5 |
| Control | 50 | 0 | 0 | 0 | 0 |

TABLE 5-continued

Test Example 3:
Test on perennial weeds in paddy field

| Compound No. | Dosage g/a | Pre-emergence Water chestnut | Pre-emergence Mizugayatsuri | Post emergence Water chestnut | Post emergence Mizugayatsuri |
|---|---|---|---|---|---|
| B | 25 | 0 | 0 | 0 | 0 |

Control B

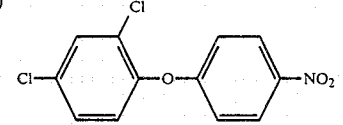

As seen in the results of Test Examples 1, 2 and 3, the compounds of the present invention showed remarkable herbicidal effect against the principal annual and perennial weeds in paddy fields in pre- and post emergence treatment.

Furthermore, it was found that the compound of the present invention showed only little phytotoxicity in pre- and post transplantation treatment.

TEST EXAMPLE 4: Pre-emergence soil surface treatment

A fixed amount of field soil was filled in a round plastic case 8 cm across and 8 cm deep, and a fixed amount of seeds of crabgrass, foxtail, pigweed, lamb's-quaters was sown followed by covering them with soil 0.5 to 1 cm thick. Then immediately a diluted solution of the compound of the present invention was applied to treat the whole surface of soil in case at a rate of 12.5 to 25 g of the compound of the present invention per are.

After the treatment the cultivation was done in a greenhouse and the herbicidal activity was observed on the 20th day. The test was carried out on 2-replication system and each average value was sought. The judging standard of the results is the same with Test Example 1. The test results are shown in Table 6.

TABLE 6

Test Example 4:
Pre-emergence treatment

| Compound No. | Dosage g/a | Crabgrass | Foxtail | Pigweed | Lamb's-quarters |
|---|---|---|---|---|---|
| 3 | 25 | 5 | 5 | 5 | 5 |
|  | 12.5 | 4 | 4.5 | 5 | 5 |
| 4 | 25 | 5 | 5 | 5 | 5 |
|  | 12.5 | 4.5 | 4.5 | 5 | 5 |
| 5 | 25 | 5 | 5 | 5 | 5 |
|  | 12.5 | 4.5 | 4.5 | 5 | 5 |
| 6 | 25 | 4.5 | 4.5 | 5 | 5 |
|  | 12.5 | 4.5 | 4 | 5 | 5 |
| 7 | 25 | 5 | 5 | 5 | 5 |
|  | 12.5 | 5 | 5 | 5 | 5 |
| 11 | 25 | 4 | 5 | 5 | 5 |
|  | 12.5 | 3 | 4.5 | 5 | 5 |
| 13 | 25 | 4 | 4 | 5 | 5 |
|  | 12.5 | 3 | 3 | 5 | 5 |
| 15 | 25 | 4 | 5 | 5 | 5 |
|  | 12.5 | 3 | 5 | 5 | 5 |
| 16 | 25 | 4 | 5 | 5 | 5 |
|  | 12.5 | 3 | 5 | 5 | 5 |
| 35 | 25 | 5 | 5 | 5 | 5 |
|  | 12.5 | 4.5 | 5 | 5 | 5 |
| 36 | 25 | 5 | 5 | 5 | 5 |
|  | 12.5 | 5 | 5 | 5 | 5 |
| 37 | 25 | 5 | 5 | 5 | 5 |
|  | 12.5 | 5 | 5 | 5 | 5 |
| Control A | 25 | 0 | 0 | 0 | 0 |
|  | 12.5 | 0 | 0 | 0 | 0 |

TABLE 6-continued

| | | Test Example 4: Pre-emergence treatment | | | |
|---|---|---|---|---|---|
| Compound No. | Dosage g/a | Herbicidal activity | | | |
| | | Crab-grass | Foxtail | Pigweed | Lamb's-quarters |
| Control B | 25 | 4 | 4.5 | 5 | 5 |
| | 12.5 | 2 | 3 | 5 | 5 |

Control A

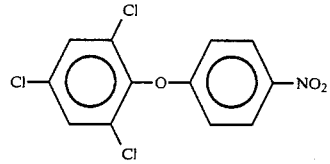

Control B

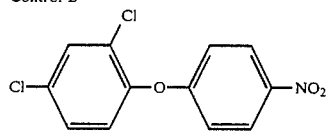

TEST EXAMPLE 5: Post emergence treatment

A fixed amount of field soil was filled in a round plastic case 8 cm across and 8 cm deep, and a fixed amount of seeds of foxtail, pigweed was sown. When they grew up to 3 to 4-leaf stage, a wettable powder containing the compound of the present invention was sprayed on the body of plants after diluting it at a rate of 12.5, 25 or 50 g of active ingredient per are.

The test was conducted on 2-replication system. Twenty days after the treatment the test results were observed on the same judging standard and the results are shown in Tables 7A and 7B.

TABLE 7A

| | Test Example 5: Post emergence treatment | | |
|---|---|---|---|
| Compound No. | Dosage g/a | Herbicidal effect | |
| | | Foxtail | Pigweed |
| 1 | 50 | 5 | 5 |
| | 25 | 4 | 5 |
| | 12.5 | 3 | 5 |
| 2 | 50 | 5 | 5 |
| | 25 | 5 | 5 |
| | 12.5 | 5 | 5 |
| 3 | 50 | 5 | 5 |
| | 25 | 5 | 5 |
| | 12.5 | 5 | 5 |
| 7 | 50 | 5 | 5 |
| | 25 | 5 | 5 |
| | 12.5 | 4.5 | 5 |
| 8 | 50 | 5 | 5 |
| | 25 | 5 | 5 |
| | 12.5 | 5 | 5 |
| 15 | 50 | 5 | 5 |
| | 25 | 5 | 5 |
| | 12.5 | 5 | 5 |
| 16 | 50 | 5 | 5 |
| | 25 | 4 | 5 |
| | 12.5 | 3 | 5 |
| 18 | 50 | 5 | 5 |
| | 25 | 4 | 5 |
| | 12.5 | 3 | 5 |
| 20 | 50 | 5 | 5 |
| | 25 | 4 | 5 |
| | 12.5 | 3 | 5 |
| 21 | 50 | 5 | 5 |
| | 25 | 5 | 5 |
| | 12.5 | 5 | 5 |
| Control A | 50 | 0 | 3 |
| | 25 | 0 | 2 |

TABLE 7A-continued

| | Test Example 5: Post emergence treatment | | |
|---|---|---|---|
| Compound No. | Dosage g/a | Herbicidal effect | |
| | | Foxtail | Pigweed |
| | 12.5 | 0 | 1 |

Control A

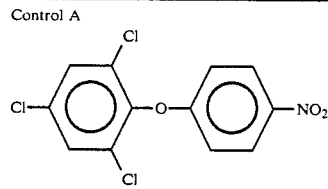

TABLE 7B

| | Test Example 5: Post emergence treatment | | |
|---|---|---|---|
| Compound No. | Dosage g/a | Herbicidal effect | |
| | | Foxtail | Pigweed |
| 29 | 50 | 5 | 5 |
| | 25 | 3 | 5 |
| | 12.5 | 2 | 5 |
| 30 | 50 | 5 | 5 |
| | 25 | 3.5 | 5 |
| | 12.5 | 3 | 5 |
| 31 | 50 | 5 | 5 |
| | 25 | 4 | 5 |
| | 12.5 | 3 | 5 |
| 32 | 50 | 5 | 5 |
| | 25 | 3 | 5 |
| | 12.5 | 2 | 5 |
| 33 | 50 | 5 | 5 |
| | 25 | 4.5 | 5 |
| | 12.5 | 3 | 5 |
| 35 | 50 | 5 | 5 |
| | 25 | 5 | 5 |
| | 12.5 | 5 | 5 |
| Control B | 50 | 5 | 5 |
| | 25 | 3 | 5 |
| | 12.5 | 2 | 4.5 |

Control B

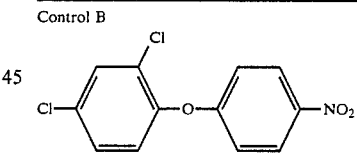

TEST EXAMPLE 6: Phytotoxicity against crops

A fixed amount of field soil was filled in a plastic vessel sized 23 cm×4.5 cm×12.5 cm and a fixed amount of seeds of soybean, cotton, corn, wheat, sunflower and rice was sown followed by 3-cm thick covering with soil.

Then immediately a diluted solution of the compound of the present invention was sprayed on the soil surface with a small sprayer at the rate of 25 to 50 g of the compound of the present invention.

After the treatment the crops were grown in a greenhouse and 20 days later the degree of phytotoxicity against each crop was observed. The test was carried out on 2-replication system and each average value was sought.

The judging standard of test results is the same with Test Example 1 and the results are shown in Table 8.

TABLE 8

| Compound No. | Dosage g/a | Test Example 6: Phytotoxicity — Phytotoxicity against crops | | | | | |
|---|---|---|---|---|---|---|---|
| | | Soybean | Cotton | Corn | Wheat | Rice | Sunflower |
| 3 | 50 | − | + | − | − | − | − |
| | 25 | − | − | − | − | − | − |
| 4 | 50 | − | − | − | − | − | − |
| | 25 | − | − | − | − | − | − |
| 5 | 50 | − | − | − | − | − | − |
| | 25 | − | − | − | − | − | − |
| 6 | 50 | − | − | − | − | − | − |
| | 25 | − | − | − | − | − | − |
| 7 | 50 | − | − | − | − | − | − |
| | 25 | − | − | − | − | − | − |
| 11 | 50 | − | − | − | − | − | − |
| | 25 | − | − | − | − | − | − |
| 13 | 50 | − | + | − | − | − | − |
| | 25 | − | − | − | − | − | − |
| 15 | 50 | − | − | − | − | − | − |
| | 25 | − | − | − | − | − | − |
| Control A | 50 | − | − | − | − | − | − |
| | 25 | − | − | − | − | − | − |

Control A

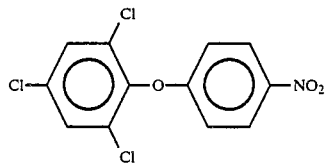

What we claim is:

1. A compound of the formula:

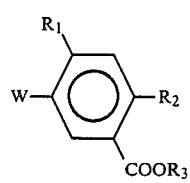

wherein W is

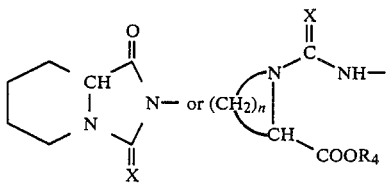

wherein $R_4$ is lower alkyl, X is oxygen or sulfur, and n is integer of 3 or 4; $R_1$ is hydrogen or halogen; $R_2$ is halogen; $R_3$ is hydrogen or $C_1$-$C_8$-alkyl which may be substituted by lower alkoxy.

2. A compound according to claim 1 wherein W is

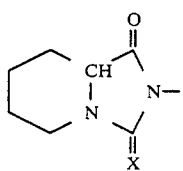

wherein X is oxygen or sulfur; $R_1$ is chloro or fluoro; $R_2$ is chloro or bromo; and $R_3$ is $C_2$-$C_4$-alkyl.

3. A compound according to claim 1 wherein W is

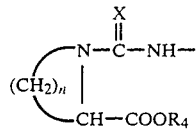

wherein $R_4$ is $C_2$-$C_4$-alkyl, n is 3 or 4 and X is oxygen or sulfur; $R_1$ is chloro or fluoro; $R_2$ is chloro or bromo; and $R_3$ is $C_2$-$C_4$-alkyl.

4. The compound as claimed in claim 2 having the formula:

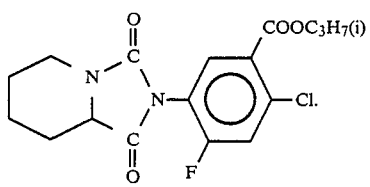

5. The compound as claimed in claim 3 having the formula:

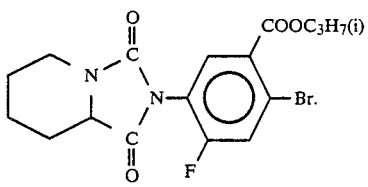

6. A herbicidal composition comprising 0.5 to 95% by weight of a compound of the formula:

(I)

wherein $R_1$, $R_2$, $R_3$ and W are defined as in claim 1 or 5 to 99.5% by weight of adjuvant(s).

7. A herbicidal composition according to claim 6 wherein W is

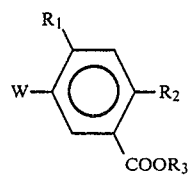

wherein X is oxygen or sulfur; $R_1$ is chloro or fluoro; $R_2$ is chloro or bromo; and $R_3$ is $C_2$-$C_4$-alkyl.

8. A herbicidal composition according to claim 6 wherein W is wherein $R_4$ is $C_2$–$C_4$-alkyl, n is 3 or 4, and X is oxygen or sulfur; $R_1$ is chloro or fluoro; $R_2$ is chloro or bromo; and $R_3$ is $C_2$–$C_4$-alkyl.

9. A method for killing weeds which comprises applying to weeds or the locus thereof a herbicidally effective amount of a compound of the formula:

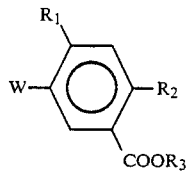
(1)

wherein $R_1$, $R_2$, $R_3$ and W are defined as in claim 1.

10. A method according to claim 9 wherein W is

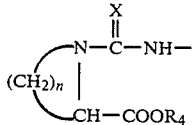

wherein X is oxygen or sulfur; $R_1$ is chloro or fluoro; $R_2$ is chloro or bromo; and $R_3$ is $C_2$–$C_4$-alkyl.

11. A method according to claim 9 wherein W is wherein $R_4$ is $C_2$–$C_4$-alkyl, and n is 3 or 4 and X is oxygen or sulfur; $R_1$ is chloro or fluoro; $R_2$ is chloro or bromo; and $R_3$ is $C_2$–$C_4$-alkyl.

* * * * *